United States Patent [19]

Stephenson

[11] 3,987,797
[45] Oct. 26, 1976

[54] ANTIMICROBIAL SUTURES
[75] Inventor: Martin Stephenson, Peterborough, Canada
[73] Assignee: Ethicon, Inc., Somerville, N.J.
[22] Filed: Dec. 11, 1974
[21] Appl. No.: 531,643

Related U.S. Application Data
[63] Continuation-in-part of Ser. No. 445,404, Feb. 25, 1974, abandoned.

[52] U.S. Cl. .............................. 128/335.5; 424/26
[51] Int. Cl.$^2$ .......................................... A61L 17/00
[58] Field of Search ............. 128/334 R, 335.5; 3/1; 106/15 AF; 260/9; 424/183, 25, 26, 78

[56] References Cited
UNITED STATES PATENTS

| | | | |
|---|---|---|---|
| 3,279,996 | 10/1966 | Long et al. .................. | 128/335.5 X |
| 3,617,344 | 11/1971 | Leininger et al. ................ | 3/1 X |
| 3,642,003 | 2/1972 | Kurtz .............................. | 128/335.5 |
| 3,674,901 | 7/1972 | Shepherd et al. ................ | 128/335.5 |
| 3,755,218 | 8/1973 | Yen et al. ........................ | 260/9 |
| 3,846,353 | 11/1974 | Grotta ............................. | 260/9 |

*Primary Examiner*—Dalton L. Truluck
*Attorney, Agent, or Firm*—Wayne R. Eberhardt

[57] ABSTRACT

A surgical suture is coated with an ionically bonded block elastomeric copolymer of a polyquaternary polyurethane and a polyanionic polymer such as heparin. The coated suture is receptive to treatment with antimicrobial compounds to produce a suture having long-lasting antimicrobial properties which inhibit bacterial growth in and immediately around the suture. The coated suture is also receptive to dyes for the preparation of colored sutures. Surgical aids other than sutures such as films, fabrics, wound dressings and the like may be coated and rendered antimicrobial or colored in a like manner.

29 Claims, No Drawings

ANTIMICROBIAL SUTURES

RELATED APPLICATIONS

This application is a continuation in part of copending U.S. application Ser. No. 445,404 filed Feb. 25, 1974 now abandoned.

BACKGROUND OF THE INVENTION

The present invention relates to antimicrobial surgical aids, particularly sutures, that have present on the surface thereof a polymer coating, particularly an antimicrobial composition that is not readily removed from the suture by leaching with water.

Germicidal sutures are described in the U.S. Pat. Nos. 861,231; 1,741,893; and 2,751,910 and more recently in patents that have issued to Dr. Leonard D. Kurtz, i.e., U.S. Pat. No. 3,642,003. South African Pat. No. 724,131 describes a suture having long-lasting germicidal properties against both gram-negative and gram-positive bacteria due to the presence within the suture of an insoluble salt of a cation of a basic antibiotic and an anion of an acid antibiotic, i.e., gentamycin oxacillinate. It is stated that such sutures, after being placed in mice for 5 days show no growth of organisms when removed and placed in a culture medium.

The Kliment et al British Pat. No. 1,248,513 and the Shepherd U.S. Pat. No. 3,632,416 and U.S. Pat. No. 3,674,901 describe coated sutures that will accept medicinal agents. But, it is a disadvantage of the suture coatings described that they have inferior mechanical properties and are easily removed from the suture.

The suture of the present invention offers an advantage over those described in South African Pat. No. 724,131 in that any anionic or cationic antimicrobial may be incorporated in the suture, and the incorporation may take place at the time of manufacture or at the time of use. Once incorporated in the suture, the antimicrobial will be retained by the suture strand over extended periods of use. Water, blood and tissue fluids slowly leach the antimicrobial compound of the suture over a prolonged period of time.

SUMMARY OF THE INVENTION

The sutures of the present invention are any conventional multifilament of monofilament suture material including for example, polyester, polypropylene, silk, cotton and linen which is coated with an ionically bonded block elastomeric copolymer of a polyquaternary polyurethane and a polyanionic polymer such as heparin. The coated suture is receptive to treatment with anionic or cationic antimicrobial compounds and/or anionic or cationic dyes. The antimicrobial treated suture is resistent to leaching and retains its antimicrobial properties in the presence of water or tissue fluid for a significant period of time to inhibit bacterial growth in and around the suture. The dyed sutures are useful for quick identification in surgical procedures where multiple sutures are employed.

DESCRIPTION OF PREFERRED EMBODIMENTS

The preferred antimicrobial surgical aids of the present invention are suture strands coated with high-heparin content polyquaternary polyurethane elastomer and then treated with selected antimicrobials. The bonding of heparin to polymers has been reported by Yen & Rembaum, J. Biomed. Mater. Res. Symposium, Vol. 1 pp 83–97 (1971). Block copolymers of polyquaternary polyurethane and heparin containing from 5 to 20 percent of heparin are described and claimed in U.S. Pat. No. 3,755,218 where such copolymers are disclosed as having non-thrombogenic characteristics and suggested for use in coating surgical devices such as membranes, tubes, catheters, valves, prosethetic veins and the like where blood clotting is of great concern. I have now found that these high-heparin content polyquaternary polyurethane elastomers are a useful substrate for retaining and slowly releasing selected antimicrobial compounds. While any of a variety of surgical aids may be rendered antimicrobial by the method of the present invention, the treatment of sutures is a particularly preferred embodiment of the present invention and the ensuing description will accordingly be directed primarily to sutures.

A preferred ionically bonded block elastomeric copolymer that functions as the coating material and the substrate for the antimicrobial compound or dye group in the present invention is described in U.S. Pat. No. 3,755,218, which patent is incorporated herein by reference. The copolymer formed between heparin and a polyquaternary polyurethane may be represented by the formula:

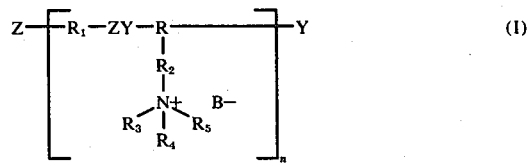

where R is $C_1$-15alkylene, $R_2$ is lower alkylene, $R_3$, $R_4$ and $R_5$ are selected from hydrogen and lower alkyl, $R_1$ is a liquid prepolymer having a molecular weight from 1,000 to 3,000 selected from the class consisting of polyether, silicone, polyurethane, and polyamide; Z and Y are selected from hydroxyl and isocyanate groups and ZY is the urethane residue of the condensation of Z and Y; n is an integer from 10 to 1,000; and B- is heparin. As used herein, lower alkyl and alkylene radicals are those containing from 1 to about 6 carbon atoms, and preferably from 1 to 4 carbon atoms.

The general reaction synthesis for the preparation of the polyquaternary polyurethane comprises reaction of a compound of the formula:

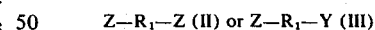

with a compound of the formula:

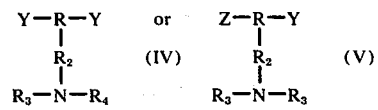

to form an intermediate non-charged or neutral polytertiary amino polymer of the formula:

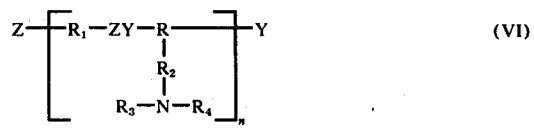

where R, $R_1$, $R_2$, $R_3$ and $R_4$ and n have the above-defined meanings.

The polymer is then reacted with a quaternizing reagent of the formula:

$$R_5A$$

where A is an anion, suitably halo, to form a polymer having the structure:

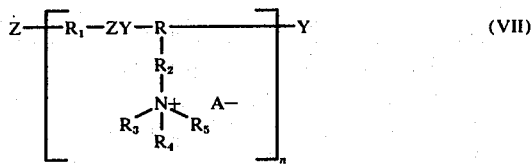 (VII)

The materials for the monomeric materials of Formula I and Formula II are preferably liquids of prepolymer length having a molecular weight above about 400 and below the range at which the prepolymer becomes excessively viscous or solid, suitably below 6,000 and preferably 1,000 to 3,000. The group $R_1$ may be an aromatic or aliphatic hydrocarbon, either saturated or unsaturated or may be a polyether, silicone (e.g., a siloxane), polyamide, polyurethane or other type of prepolymer.

The Z and Y groups are selected from condensation coreactants generally utilized in forming condensation resins such as isocyanate-hydroxyl (urethane) isocyanate-amine (urea), hydroxyl-carboxyl (polyester) amino-carboxyl (amide) and the like. Urethane linking reactants are preferred due to the ready availability of diverse polyisocyanate materials, the absence of elimination products and the ready ability to select and control the properties of the final prepolymer.

Examples of suitable monomeric diisocyanates include benzene-1,3-diisocyanate, hexane-1,6-diisocyanate, tolylene-2,4-diisocyanate (TDI), tolylene-2,3-diisocyanate, diphenylmethane-4,4-diisocyanate, naphthalene-1,5-diisocyanate, diphenyl 3,3'-dimethyl-4,4'-diisocyanate, diphenyl-3,3'-dimethoxy-4,4'-diisocyanate diethyl ether, 3 (diethylamino)-pentane-1,5-diisocyanate, butane-1,4-diisocyanate, cyclohex-4-ene-1,2-diisocyanate, toluidine diisocyanate, isocyanate terminated prepolymers, polyaryl diisocyanates, and the like. Suitable commercially available higher molecular weight liquid polyisocyanates are Adiprene L-100 (DuPont), an isocyanate terminated polybutylene oxide having a molecular weight of about 2,000 and Adiprene L-167 (DuPont), an isocyanate terminated polybutylene oxide having a molecular weight of about 1,350.

Terminally reactive liquid polymers, such as hydroxy terminated polybutadienes containing 20 to 500 or more carbon atoms or Bis-phenol A terminated liquid polysiloxanes can be converted to diisocyanates by reaction with a diisocyanate such as haxe-methylene diisocyanate. As the carbon chain length of the prepolymer increases, elastomeric properties are favored.

The $R_1$ group in the monomeric compounds of Formulas III and IV may also be aliphatic, aromatic or the various prepolymers discussed above. In the case of the use of a prepolymer diisocyanate the hydroxy amine material is suitably a compound of the formula:

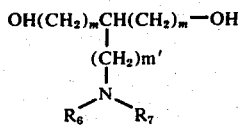

where $R_6$ and $R_7$ are lower alkyl, aryl such as phenyl, aralkyl such as benzyl or lower alkenyl, and each $m$ is individually an integer from 0 to about 6 and $m'$ is an integer of from 1 to about 6. Exemplary compounds are 3-dimethylamino-1,2-propane diol, 4-diethylamino-1,3-butane diol, 6-dimethylamino-1,4-hexane diol.

In the quaternizing reagent $R_5A$, $R_5$ may be hydrogen or lower alkyl, and A may be halo such as chloro, bromo or iodo, alkyl sulfate such as methyl sulfate, or alkyl iodide such as methyl iodide.

The polymerization reaction may be conducted in bulk or in the presence of a solvent for the monomers and polymer product such as benzene. The reaction may be conducted at room temperature or at elevated temperature up to or above the reflux temperature. The quaternization reaction is conducted in the presence of a solvent for the tertiary amino polymer and for the resulting quaternary salt such as tetrahydrofuran, acetone, dioxane, dimethylformamide, diaminoheptane, or mixtures thereof.

The quaternized elastomeric polymer are further reacted with anionic polymers or salts thereof such as polystyrene sulfonate, polyacrylates and the like and particularly with heparin or its alkali metal or ammonium salts to form viscoelastic ionically linked block polymeric salts of the formula:

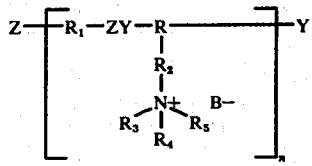

wherein B- is an anionic polymer preferably heparin, and R - $R_5$, Z, Y and $n$ are as defined above.

The heparin content of the block polymer can be varied between 5% to about 20% by weight. Higher heparin content materials can be prepared but are found to have a lower degree of elasticity. Lower heparin content materials are soluble in common organic solvents while materials containing above 15% heparin are soluble in polar solvents such as THF, dimethylformamide (DMF), hexamethyl phosphoramide (Hexametapol) and especially mixtures thereof with 1-methyl-2-pyrrolidone. For the highest heparin content materials a small amount of about 0.01% to 5% of a primary or secondary amine such as dibutylamine in DMF is necessary to achieve complete solubility.

The block polymer forms by anionic reaction of the quaternized elastomer, (chloride counterion), with sodium heparin with elimination of sodium chloride. Hence, the amount of chloride after reaction is very low. The reaction is conducted simply by combining the elastomer with sodium heparin preferably as separate solutions in solvent, suitably in 50:50 by volume mixtures of methanol and water.

Copolymers of the polyquaternary polyurethane and anionic polymer to which an anionic or cationic antimicriobial compound or dye group has been subsequently attached as hereinafter described are conveniently represented by the structure:

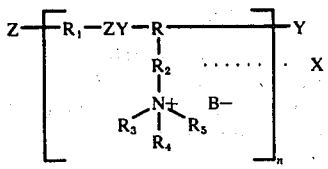

wherein X is said antimicrobial compound or dye group.

The attachment of the antimicrobial or dye group to the heparin elastomer is represented in the formula with a dotted line because the true mechanism of bonding is not known. While not wishing to be bound by theory, according to one possible mechanism the heparin elastomer may contain free positively charged nitrogen atoms and free negatively charged sulpho groups which are available for binding anionic (X —) or cationic (X +) antimicrobial or dye groups. Under another possible mechanism, the addition of the antimicrobial agent or dye group may result in dissociation of the heparin elastomer with precipitation and/or entrapment of the heparin-antimicrobial or heparin-dye complex within the polymer matrix. While either or both of these mechanisms may occur, or some other mechanism may be involved, knowledge of the true mechanism is not essential to understanding or operating the present invention.

The polyquaternary polyurethane-heparin copolymer will retain basic antimicrobials such as gentamycin or benzethonium chloride and acid antibiotics such as the penicillins. Other examples of suitable antimicrobials which are retained by the high-heparin content polyquaternary polyurethane elastomers and slowly released after implantation of the suture are the cephalosporins such as cephalolexin, cephaloglycin, cephaloridine, cephalothin; the 6-substituted penicillanic acids such as penicillins G, N and V, methicillin, oxacillin; and also vancomycin, neomycin, erythromycin, streptomycin, cycloserine, tetracycline, aureomycin, terramycin (oxtetracycline) gentamycin, and polymyxin B. Particularly preferred is neomycin sulfate.

The base fiber to which the elastomeric heparin polymer coating is applied may be any non-absorbable suture material such as nylon, silk, polyester, and cotton or any absorbable suture material, such as catgut and homopolymers and copolymers of glycolide and lactide.

While any base fiber may be coated with the elastomeric heparin polymer, the adhesion of the coating to a fiber such as polypropylene is relatively poor, and the applications of such coated fibers are to be limited accordingly.

The elastomeric polymer is dissolved in a suitable solvent and applied to the suture material from solution. In a preferred method, the suture is immersed in a solution containing from about 1.0 to about 50% by weight of the polymer, and preferably from about 3 to about 30 percent in dimethylformamide solvent. The suture is dried to remove the solvent and leave a uniform residual coating of elastomeric heparin polymer. Successive coatings may be applied by reimmersing and reapplying the suture any number of times until the desired level of polymer addition is achieved. In general, from 0.1 to 25 percent of polymer by weight of the suture constitutes an effective range of polymer addon. Greater or lesser amounts of polymer may of course be beneficially used although amounts in excess of 25 percent may result in stiffening of the suture and in some adhesion between adjacent strands when the suture is spooled.

The coated suture is capable of accepting a wide range of antimicrobials. The coated suture may be sterilized, packaged, and held in such neutral form until ready for use at which time a selected antimicrobial may be easily applied. Such a suture makes possible the selection of the most effective antimicrobial for use in a particular case.

Alternatively, the suture may be treated with a selected antimicrobial, sterilized and packaged and stored for later use. In the event the selected antimicrobial is adversely affected by the suture sterilization technique the coated suture may be sterilized prior to the application of a sterile antimicrobial, and the treated suture packaged under antiseptic conditions. Such mechanical procedures are conventional and well within the ability of those skilled in the art. Sterilization for example, may be by exposure to ethylene oxide or cobalt 60 radiation or other conventional means.

The selected antimicrobial is conveniently applied to the coated suture from aqueous solution. The coated suture is simply immersed in the solution for a period of a few seconds to several minutes or longer, then removed and either dried or used "as is", without drying. The concentration of antimicrobial in the treating solution may vary according to solubility of particular compounds but concentrations in the range of from about 1.0 to 10 percent by weight are generally satisfactory although lesser or greater concentrations may be used if desired.

The elastomeric heparin polymer may also be applied to any prosthetic device useful in surgical applications where a surgical aid or support is required, i.e., heart valves, woven or extruded tubular structures having use in the repair or arteries, veins, ducts, asophagi; woven or knitted fabrics useful surgically in hernia repair and in supporting damaged liver, kidney, and other internal organs; pins, screws, reinforcing plates, and artificial tendons or cartilage material. Antimicrobial compositions applied to the surface of surgical aids that have been so treated are retained by the elastomeric heparin polymer and slowly released.

Other surgical aids on which the elastomeric heparin polymer may also be used as a coating include bandages and other wound dressings designed for topical applications. Alternatively, the polymer may be cast as a thin polymeric film, sterilized, and packaged for use as a wound dressing. As in the case of sutures, the antimicrobial material may be incorporated in the elastomeric heparin polymer at the time of manufacture or at the time of use. In addition to the antimicrobial, a local anesthetic such as cinchocaine hydrochloride may also be applied to the surface of the elastomeric coating or film.

The polyquaternary polyurethane heparin polymer coated sutures are also receptive to anionic and cationic dyes and may accordingly be dyed a wide range of colors. The dyes may be applied alone or in conjunction with one or more antimicrobial compounds. The dyes are conveniently applied to the suture from aqueous solutions at ambient temperature by immersion, padding, spraying or the like.

The following examples are presented solely for the purpose of illustration. It is to be understood that many alternative, equivalent reactants and conditions may readily be substituted by those skilled in the art. Antimicrobial activity of the sutures of this invention were evaluated in vitro in accordance with the following test procedure:

Standard Testing Procedure for Assessing the
In Vitro Efficacy of Antimicrobial Sutures Organisms: Bacillus subtilis ATCC 19659
Escherichia coli ATCC 10536
Pseudomonas aeruginosa ATCC 15442
Staphylococus aureus ATCC 6835
Media: Tryptic soy broth (Difco) + 0.4% Ion Agar 2 S Procedure 1. Plates of tryptic soy agar (Difco) were streaked with the appropriate organism and incubated overnight at 37° C. Cells were washed from the surface by means of glass beads and saline. The optical density of each suspension was adjusted to 0.1.

2. Tubes of tryptic soy broth + 0.4% Ion Agar 2 S were equilibrated to a temperature of 45°–50° C in a water bath. Ten percent (or 2.5 ml/25 ml tryptic soy broth + 0.4% Ion Agar 2 S) bovine serum and 1 percent (or 0.25 ml) of the adjusted bacterial suspension were pipetted into the media and mixed by slow vortexing or by hand. Eight milliliters of this seeded media were pipetted per plate and allowed to cool.

3. 1.5 centimeter pieces of potential antimicrobial sutures were then placed on the cool agar and incubated 24 hours at 37° C. Each test was performed in triplicate. No more than four pieces of antimicrobial suture were positioned on each plate, equidistant from the edges and the center. After incubation, accurate zone measurements were obtained, using vernier calipers. Measurements were taken of the total zone width at right angles to the longitudinal axis of the suture and included the suture diameter.

EXAMPLE 1

Fifty grams of ADIPRENE L 167 (a polybutylene oxide diisocyanate commercially available from E. I. DuPont de Nemours & Co., Inc., Wilmington, Delaware 19898; containing between 6.15 and 6.55 percent of available isocyanate) is dissolved in 500 ml. benzene and reacted with 4.6 grams of vacuum distilled 3-methylamino-1,2-propane diol at refluxing temperature for 48 hours. The reaction is followed by means of I.R. spectra. The disappearance of the OH peak at $\lambda = 3480$ cm$^{-1}$ as well as the NCO absorption peak at $\lambda = 2280$ cm$^{-1}$ indicates completion of the reaction. At the end of 48 hours, 300 ml. of benzene is distilled from the reaction flask and the residue freeze dried to remove all residual benzene. The yield of the condensation product is 56.2 grams.

EXAMPLE 2

Thirty grams of the condensation product of Example 1 is dissolved in 200 ml. of tetrahydrofuran. A concentrated solution of hydrochloric acid (8 grams of 37–38 percent HCl by weight) is added corresponding to a 100 percent stoichiometric excess. The solution is stirred at room temperature overnight and then precipitated with 1500 ml. of n-hexane. It is then washed thoroughly with water to remove unreacted HCl. The quaternized polymer is dried in vacuum at 50° C. overnight.

EXAMPLE 3

Twenty-five grams of the quaternized polymer described in Example 2 above is dissolved in 250 ml. of methanol. Distilled water (150 ml.) is added to this mixture slowly with stirring to form a homogeneous solution (Solution A).

Five grams of sodium heparin is dissolved in 125 ml. of distilled water. To this solution is added slowly with stirring 175 ml. of methanol to produce a homogeneous heparin solution (Solution B). The polymer solution (Solution A) is added quickly to the heparin solution (Solution B) with vigorous stirring. The resulting precipitate is collected, washed with water, and vacuum dried at room temperature. The yield after drying is 6.2 grams. The heparin content of this product is 16 percent by weight.

EXAMPLE 4

Sixty feet of a size 2/0 strand of polyester fiber suture is treated on a laboratory coating machine with a solution of 0.5 parts by weight of the heparin polymer prepared in Example 3 above in 15 parts by weight of dimethylformamide. The coated suture strand, after drying, contains 7.2 percent by weight of polymer and has good handling and tie-down properties.

A portion of the coated suture material is immersed for 1 hour in a solution obtained by dissolving 2.5 parts streptomycin sulfate in 50 parts distilled water. The suture is then removed, placed in a flask, and extracted by agitating with distilled water as follows:

(i) 500 ml. distilled water for 15 minutes
(ii) 500 ml. distilled water for 15 minutes      Agitated by
(iii) 500 ml. distilled water for 15 minutes      swirling
(iv) 500 ml. distilled water overnight 17 hours
(v) Rinsed briefly under running distilled water.

The suture is then dried, sterilized by cobalt-60 radiation and tested for in vitro antimicrobial activity. For comparison, two control polyester fiber sutures were included. One was not coated with the high-heparin elastomer, but otherwise treated in exactly the same way. The second control was a polyester fiber suture, coated with the high-heparin content elastomer of Example 3 without further treatment. The table below summarizes the results. Zones of inhibition are measured in centimeters.

| Suture Material | B. subtilis | E. coli | Ps. aeruginosa | S. Aureus |
|---|---|---|---|---|
| Suture coated with high-heparin elastomer. Treated in aqueous streptomycin sulfate. Extracted with distilled water as described above. | 0.55 | 0.19 | no zones | 0.44 |
| Suture uncoated control Treated in aqueous streptomycin sulfate. Extracted approx. 18 hours with distilled water. | no zones | no zones | no zones | no zones |
| Suture coated with high heparin elastomer. | no zones | no zones | no zones | no zones |

-continued

| Suture Material | B. subtilis | E. coli | Ps. aeruginosa | S. Aureus |
|---|---|---|---|---|
| No further treatment. | | | | |

After 7-day implantation in rats, no significant differences in tissue reaction were seen in any of the above-listed sutures.

EXAMPLES 5 – 12

The procedure of Example 4 is repeated substituting different anionic and cationic antimicrobial compounds for the streptomycin sulfate of Example 4. Examples 5–7 used the same coated suture as used in Example 4. Examples 8–12 used an identical suture except for a slightly lower level of coating. The efficiency of the various antimicrobial compounds after water extraction is apparent from the following data.

| Example | Coating Wt. % | Antimicrobial | Mean size (cm) of Zone of Inhibition | | | |
|---|---|---|---|---|---|---|
| | | | B.S. | E.C. | P.A. | S.A. |
| 5 | 7.2 | neomycin sulfate | 1.78 | 0.99 | 0.42 | 1.25 |
| 6 | 7.2 | tetracycline hydrochloride | 1.78 | 0.58 | 0 | 1.19 |
| 7 | 7.2 | potassium penicillin | 0.28 | 0 | 0 | 0.85 |
| 8 | 6.8 | gentamycin sulfate | 1.44 | * | * | * |
| 9 | 6.8 | oxytetracycline dihydrate | 0.30 | * | * | * |
| 10 | 6.8 | polymixin B sulfate | 0.29 | * | * | * |
| 11 | 6.8 | sodium cephalothin | 1.48 | * | * | * |
| 12 | 1.0 | neomycin sulfate | 1.12 | * | * | * |

*Not evaluated
B.S. = *Bacillus subtilis*
E.C. = *Escherichia coli*
P.A. = *Pseudomonas aeruginosa*
S.A. = *Staphylococcus aureus*
In all of these Examples 5-12, a similarly treated but uncoated suture control gave no zone of inhibition.

EXAMPLE 13

A sample of the coated suture treated with neomycin sulfate of Example 5 was subjected to a prolonged series of water extractions in 1.5 liter quantities of distilled water as follows:
9 — 24 hour extractions
1 — 120 hour extractions
3 — 168 hour extractions At the end of these extractions, the treated suture produced a zone of inhibition of 1.26 cm against *Bacillus subtilis*. A similarly treated but uncoated control demonstrated no antimicrobial properties after an initial 24 hour extraction.

EXAMPLES 14 – 21

A series of tests were run using a modified extraction technique on sutures treated with antimicrobials, some of which were more susceptible to water extraction than those of the previous examples. In all of the following examples, the suture was a braided polyester size 2-0 which had been coated with about 7% by weight of the heparin polymer according to the method of Example 4. The sutures were cobalt sterilized and then immersed in a 5% aqueous solution of the selected antimicrobials for 1 hour at room temperature. The treated sutures were evaluated for antimicrobial activity before extraction and after periods of 1, 2 and 4 hours extraction in distilled water. The following data were obtained.

| Example | Antimicrobial | Mean Size (cm) of Zone of Inhibition | | | |
|---|---|---|---|---|---|
| | | Extraction- 0 | 1 hr. | 2 hr. | 4 hr. |
| 14 | Neomycin sulfate | 1.62 | 0.74 | 0.71 | 0.70 |
| 15 | Rifamycin | 1.79 | 1.24 | 1.24 | 0.89 |
| 16 | Benzethonium chloride | 1.39 | 0.76 | 0.71 | 0.67 |
| 17 | Cephaloridine | 3.77 | 1.19 | 0.58 | 0.13 |
| 18 | Sodium oxacillin | 2.91 | 0.62 | 0 | 0 |
| 19 | Dihydro streptomycin sulfate | 1.71 | 0.23 | 0 | 0 |
| 20 | Disodium carbenicillin | 2.31 | 0.20 | 0 | 0 |
| 21 | Sodium furadantin | 1.15 | 0 | 0 | 0 |

It is apparent from the above data that some antimicrobials are more susceptible to water leaching than others. With the exception of Example 21 however, all sutures demonstrated some antimicrobial action after 1 hour extraction, and such sutures are considered to possess a significant degree of durable antimicrobial activity.

EXAMPLE 22

Healthy young adult Sprague-Dawley rats were anesthetized, hair was removed from their backs with clippers and the skin prepared for surgery. Under sterile conditions, a 6 inches strand of the suture material of Example 5 was inserted with a small hemostat through a 0.5 cm incision in the dorsal subcutis on the right side. An antimicrobial treated but uncoated control strand was placed on the left side. The incisions were closed and the rats returned to their suitably identified cages.

At appropriate time intervals, animals were sacrificed with carbon dioxide, the dorsal skin dissected and the exposed sutures removed aseptically. With a separate set of dry, sterile forceps and scissors for each separate strand, the outermost ends of the strand (ca. ¼ inch) were cut off and discarded. The remaining strand was cut into 1.5 cm pieces and, without resterilization, tested for residual antimicrobial activity by the in vitro method described above using *B. subtilis* as the indicator organism. The test results presented in the table below clearly indicate the long lasting antimicrobial effect obtained with the coated sutures of this invention.

| Implantation Time (Days) | Zones of Inhibition (cm) | |
|---|---|---|
| | Suture of Example 13 | Uncoated Control |
| 0 (non-implanted) | 2.09 | 2.22 |
| 3 | 0.31 | no zones |
| 7 | 0.46 | no zones |
| 14 | 0.44 | no zones |
| 21 | 0.14 | no zones |
| 28 | 0.04 | no zones |

EXAMPLE 23

Braided nylon suture (size 2/0, undyed, not waxed) was coated with the heparin polyquaternary polyurethane elastomer as described in Example 4. After three passes through the coating apparatus, the polymer add-on was found to be 8.01% based on weight of suture.

A 20 cm length of the coated nylon suture was soaked in 5% w/v neomycin sulphate solution for 1 hour at room temperature. After removal, the strand was washed in three separate 500 ml quantities of distilled water, 15 minutes in each wash and then allowed to soak in 500 ml distilled water overnight. The strand was then held under running distilled water for several seconds and dried at room temperature.

Portions of the suture were then tested for residual antimicrobial activity using *B. subtilis* as the test organism. The mean of zones of inhibition was 1.44 cm. For comparison, a normal uncoated sample of nylon suture was soaked in neomycin sulphate solution and then washed with water under exactly the same conditions as were used for the coated suture. This control suture gave no zones of inhibition against the test organism.

EXAMPLE 24

Braided silk suture (size 2/0, undyed, not waxed) was treated with two coats of polymer solution, in a similar way to the procedure in Example 23. Polymer add-on was 2.83% based on suture weight. Treatment in 5% neomycin sulphate solution followed by water extraction was carried out exactly as described in Example 23. Mean zone of inhibition against the test organism *B. subtilis* was found to be 2.06 cm.

For comparison, a control silk suture without polymer coating, but otherwise similarly treated in neomycin sulphate solution followed by water extraction was found to give a mean zone of inhibition of 2.09 cm.

EXAMPLE 25

One gram of the heparin elastomer described in Example 3 is dissolved in 20 ml. of dimethylformamide, 2 ml. of dibutylamine, and 1 ml. of hexamethylphosphoromide, and cast as a thin film on a glass surface. The solvent is removed at 100° C. in an oven and the film peeled away from the smooth glass surface. The film is soaked in an aqueous (4 percent by weight) of tetracycline hydrochloride, air dried at room temperature, packaged and sterilized with cobalt-60 radiation. The thin films so obtained are useful for dressing skin wounds and burns.

EXAMPLE 26

Braided polyester suture (size 2/0 white) was coated with heparin polymer as described in Example 4. The coated suture was sterilized by cobalt-60 in a conventional manner, and portions of the coated fiber were immersed in various dye solutions described below. A section of uncoated suture was included in each dye test as a control. Samples were removed from the dye bath, rinsed and evaluated for color. The following results were obtained.

| Dye Solution | Coated Suture | Uncoated Control |
|---|---|---|
| Rhodamine B (0.1 gm in 20 ml distilled water) | Deep pink | Faintly tinged with pink |
| Bromothymol Blue (0.1 gm in 20 ml distilled water) | Yellow | Colorless |
| Methylene Blue (0.1 gm in 20 ml distilled water) | Dark blue | Faintly tinged with blue |
| Eriochrome Black T (0.1 gm in 20 ml distilled water) | Reddish brown | Colorless |
| Bromocresol Green (0.1 gm in 20 ml distilled water insol.residue filtered off) | Green | Colorless |
| Azure A (0.1 gm in 20 ml distilled water, insol. residue filtered off) | Deep violet | Faintly tinged with blue |
| Quinizarin Sulphonic Acid (0.1 gm in 20 ml distilled water, 10 drops 0.1 NaOH solution added, insol. residue filtered off) | Orange brown | Colorless |
| Thymol Blue (0.1 gm in 20 ml distilled water, 10 drops of 0.1N NaOH solution added, insol. residue filtered off) | Yellow | Colorless |
| Pararosaniline Hydrochloride (0.1 gm in 20 ml distilled water, 10 drops of 0.1N NaOH solution added, insol. residue filtered off) | Deep violet | Faintly tinged with blue |

The following dyes were evaluated in a like manner. In all cases, the fibers coated in accordance with the instant invention were colored to a pale to medium shade, while the uncoated fibers showed no appreciable coloration: phenol red, uranine, paraxylenol blue, haematein, methyl orange, methyl red, disodium salt of phenolphthalein, and bromophenol blue.

While the foregoing examples have described a preferred embodiment of the present invention wherein the suture coating comprised a copolymer of polyquaternary polyurethanes and heparin, these examples are for purposes of illustration only and are not limiting of the invention. Numerous substitutions, modifications and alternatives in polymer compositions, antimicrobial compounds and dye compounds will be apparent to those skilled in the art and may be employed without departing from the scope of the invention described in the following claims.

What is claimed is:

1. A surgical aid having long-lasting, leach resistant antimicrobial properties the surface of which is coated with an ionic block elastomer of the formula:

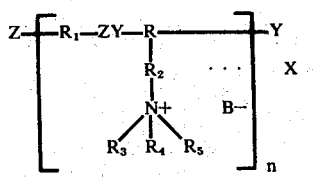

wherein R is $C_1$-15 alkylene, $R_2$ is lower alkylene, $R_3$, $R_4$ and $R_5$ are selected from hydrogen and lower alkyl, $R_1$ is a liquid prepolymer having a molecular weight from 1,000 to 3,000 selected from the class consisting of polyether, silicone, polyurethane, and polyamide; Z and Y are selected from hydroxyl and isocyanate groups, ZY is the urethane residue of the condensation of Z and Y; $n$ is an integer from 10 to 1,000; B- is an anionic polymer and X is an anionic or cationic antimicrobial compound.

2. A surgical aid of claim 1 wherein the anionic polymer is selected from the group consisting of polystyrene sulfonate, polyacrylate and heparin.

3. A surgical aid of claim 1 wherein the antimicrobial compound is selected from the group consisting of neomycin sulfate, tetracycline hydrochloride, potassium penicillin, streptomycin sulfate, gentamycin sulfate, oxtetracycline dihydrate, polymixin B sulfate, sodium cephalothin, rifamycin, benzethonium chloride, cephaloridine, sodium oxacillin, dihydrostreptomycin sulfate, and disodium carbenicillin.

4. A surgical aid of claim 3 wherein the anionic polymer is heparin.

5. A surgical aid of claim 1 which is a suture.

6. A surgical aid of claim 1 which is a wound dressing.

7. A surgical aid of claim 1 which is a fabric.

8. A surgical aid of claim 1 which is a prosthetic device.

9. A suture of claim 5 wherein B- is heparin and X is neomycin sulfate.

10. A colored surgical aid, the surface of which is coated with an ionic block elastomer of the formula:

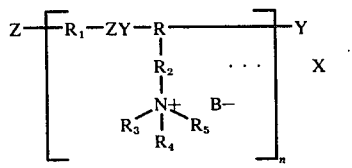

wherein R is $C_1$-15 alkylene, $R_2$ is lower alkylene, $R_3$, and $R_4$ and $R_5$ are selected from hydrogen and lower alkyl, $R_1$ is a liquid prepolymer having a molecular weight from 1,000 to 3,000 selected from the class consisting of polyether, silicone, polyurethane, and polyamide; Z and Y are selected from hydroxyl and isocyanate groups, ZY is the urethane residue of the condensation of Z and Y; $n$ is an integer from 10 to 1,000; B- is an anionic polymer and X is an anionic or cationic dye group.

11. A surgical aid of claim 10 wherein the anionic polymer is selected from the group consisting of polystyrene sulfonate, polyacrylate and heparin.

12. A surgical aid of claim 10 which is a suture.

13. A surgical aid of claim 10 which is a wound dressing.

14. A surgical aid of claim 10 which is a fabric.

15. A suture of claim 12 wherein B- is heparin.

16. A sterile surgical suture, the surface of which is coated with an ionic block elastomer of the formula:

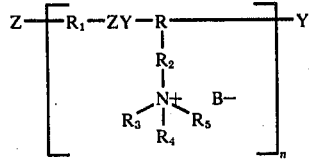

wherein R is $C_1$-15 alkylene, $R_2$ is lower alkylene, $R_3$, $R_4$ and $R_5$ are selected from hydrogen and lower alkyl, $R_1$ is a liquid prepolymer having a molecular weight from 1,000 to 3,000 selected from the class consisting of polyether, silicone, polyurethane, and polyamide; Z and Y are selected from hydroxyl and isocyanate groups, ZY is the urethane residue of the condensation of Z and Y; $n$ is an integer from 10 to 1,000; and B- is an anionic polymer.

17. A surgical suture of claim 16 wherein the anionic polymer is selected from the group consisting of polystyrene sulfonate, polyacrylates, heparin.

18. A surgical suture of claim 16 whrein the anionic polymer is heparin.

19. A method of preparing an antimicrobial surgical aid comprising the steps of contacting the surface of a surgical aid with a solution of an ionic block elastomer of the formula:

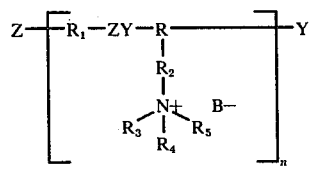

wherein R is $C_1$-15 alkylene, $R_2$ is lower alkylene, $R_3$, $R_4$ and $R_5$ are selected from hydrogen and lower alkyl, $R_1$ is a liquid prepolymer having a molecular weight from 1,000 to 3,000 selected from the class consisting of polyether, silicone, polyurethane, and polyamide; Z and Y are selected from hydroxyl and isocyanate groups, ZY is the urethane residue of the condensation of Z and Y, $n$ is an integer from 10 to 1,000 and B- is an anionic polymer, drying said surgical aid to leave a residual coating of said ionic block elastomer thereon, and thereafter contacting said coated surgical aid with an anionic or cationic antimicrobial compound.

20. A method of claim 19 wherein the anionic polymer is selected from the group consisting of polystyrene sulfonate, polyacrylates, heparin.

21. A method of claim 19 wherein said solution of ionic block elastomer comprises an organic solvent.

22. A method of claim 21 wherein said organic solvent comprises dimethylformamide.

23. A method of claim 19 wherein said coated surgical aid is contacted with an aqueous solution of said antimicrobial compound.

24. A method of claim 19 wherein said anionic polymer is heparin.

25. A method of claim 24 wherein said antimicrobial compound is neomycin sulfate.

26. A method of claim 25 wherein said surgical aid is a suture.

27. A method of claim 25 wherein said surgical aid is a wound dressing.

28. A method of claim 25 wherein said surgical aid is a fabric.

29. A method of claim 25 wherein said surgical aid is a prosthetic device.

* * * * *

UNITED STATES PATENT OFFICE
CERTIFICATE OF CORRECTION

Patent No. 3,987,797  Dated October 26, 1976

Inventor(s) Martin Stephenson

It is certified that error appears in the above-identified patent and that said Letters Patent are hereby corrected as shown below:

In Column 4, Line 44, "anionic polymer preferably heparin and" should read --- anionic polymer, preferably heparin, and ---.

In Column 5, Line 46, "(oxtetracycline)" should read --- (oxytetracycline) ---.

In Column 5, Line 47, "polymyxin" should read --- polymixin ---.

In Column 6, Line 43, "in the repair or" should read --- in the repair of ---.

In Column 7, Line 16, "Staphylococus" should read --- Staphylococcus ---.

In Column 10, Line 33, "inches" should read --- inch ---.

In Claim 3, Line 16, "oxtetracycline" should read --- oxytetracycline ---.

UNITED STATES PATENT OFFICE
CERTIFICATE OF CORRECTION

Patent No. 3,987,797  Dated October 26, 1976

Inventor(s) Martin Stephenson

It is certified that error appears in the above-identified patent and that said Letters Patent are hereby corrected as shown below:

In Claim 17, Line 20, " ,heparin" should read --- , and heparin ---.

In Claim 18, Line 21, "whrein" should read --- wherein ---.

In Claim 20, Line 48, " ,heparin" should read --- , and heparin ---.

Signed and Sealed this second Day of August 1977

[SEAL]

Attest:

RUTH C. MASON
Attesting Officer

C. MARSHALL DANN
Commissioner of Patents and Trademarks